United States Patent [19]

Vargiu et al.

[11] 4,017,523

[45] Apr. 12, 1977

[54] PROCESS FOR THE CONTINUOUS PREPARATION OF POLYGLYCIDYL ETHERS OF POLYHYDROXY PHENOLS

[75] Inventors: Silvio Vargiu, Sesto S. Giovanni (Milan); Giancarlo Crespolini, Bergamo; Giulio Grazzini, Cinisello Balsamo (Milan), all of Italy

[73] Assignee: Societa' Italiana Resine S.I.R. S.p.A., Milan, Italy

[22] Filed: May 30, 1975

[21] Appl. No.: 582,518

[30] Foreign Application Priority Data

May 30, 1974 Italy .................................. 23314/74

[52] U.S. Cl. ............................................ 260/348.6
[51] Int. Cl.² ....................................... C07D 301/28
[58] Field of Search ................................ 260/348.6

[56] References Cited

UNITED STATES PATENTS 2,841,595  7/1958  Pezzaglia ......................... 260/348.6
3,069,434  12/1962  Spence et al. .................... 260/348.6

OTHER PUBLICATIONS

Chemical Abstracts, vol. 60 (1964) 5704 g.

*Primary Examiner*—Norma S. Milestone
*Attorney, Agent, or Firm*—Sughrue, Rothwell, Mion, Zinn & Macpeak

[57] ABSTRACT

Liquid epoxy resins are produced by contacting a dihydroxy phenol with an excess of epihalohydrin and an aqueous solution of an alkali metal hydroxide in a molar ratio of hydroxide to phenol not exceeding 2:1, recovering from the reaction products an epoxy resin having a content of hydrolyzable chlorine of from 1 to 6% by weight, contacting a solution of the resin in a hydrocarbon with an aqueous solution of an alkali metal hydroxide while maintaining an atomic ratio of alkali metal to hydrolyzable chlorine contained in the resin of from 1:1 to 1.17:1 and recovering from the reaction products a liquid epoxy resin having a content of hydrolyzable chlorine less than 0.02% by weight.

These epoxy resins of high purity are particularly useful as varnishes or coatings.

8 Claims, 1 Drawing Figure

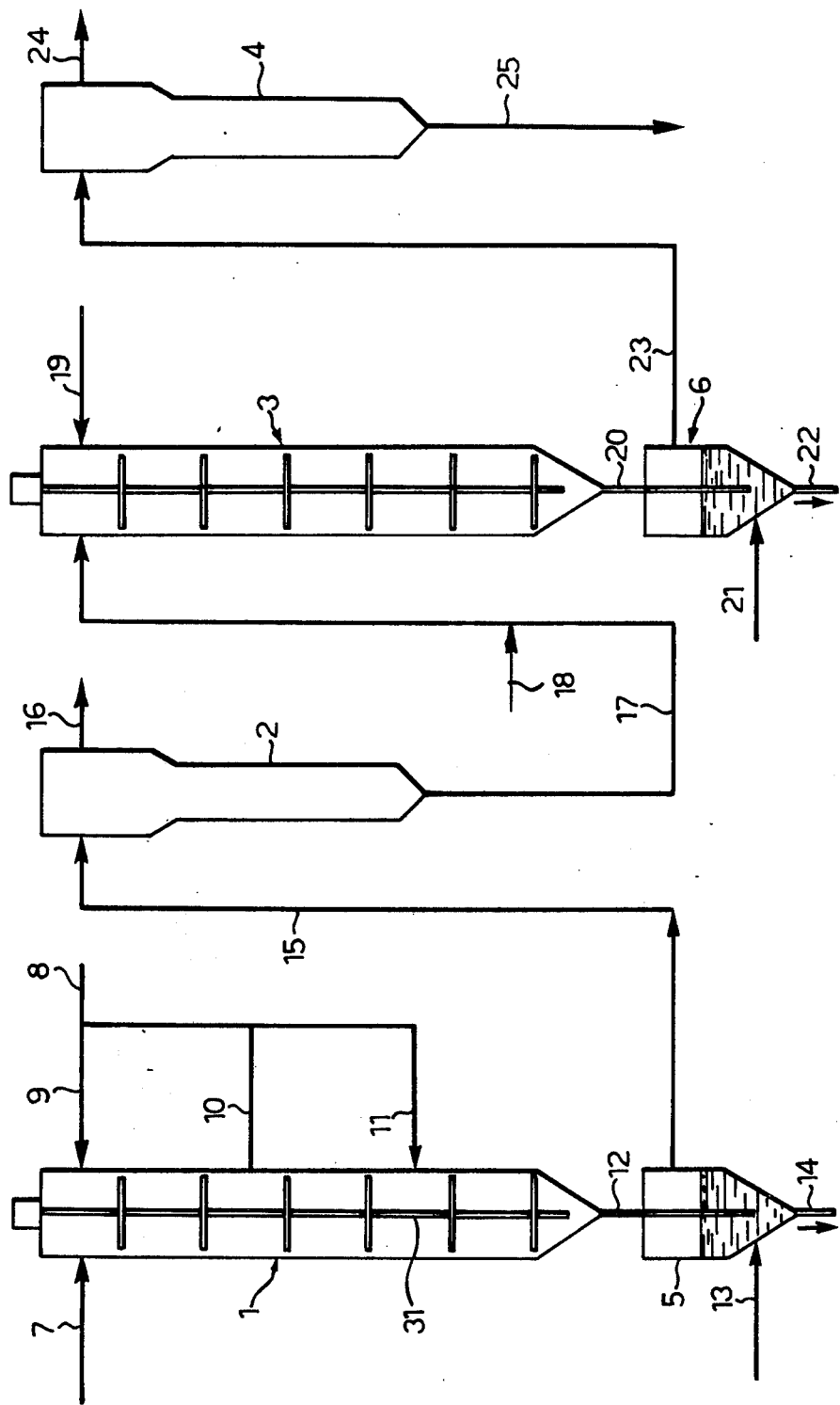

PROCESS FOR THE CONTINUOUS PREPARATION OF POLYGLYCIDYL ETHERS OF POLYHYDROXY PHENOLS

BACKGROUND OF THE INVENTION

1. Field of the Invention

The present invention relates to the preparation of polyglycidyl ethers of polyhydroxy phenols, by means of a continuous process.

In particular, the invention relates to the reaction of an epihalohydrin with a dihydroxy phenol to form the diglycidyl ether of the dihydroxy phenol of the following formula:

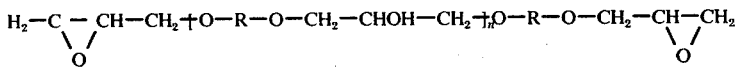

(in which O-R-O is a dihydroxy phenol group and $n$ is a number close to zero or even zero, i.e. $n$ usually does not exceed an average value of 0.2) in which the halogen content is reduced to a trace, especially the hydrolyzable halogen content.

The preparation of diglycidyl ethers of dihydroxy phenols will be further described with reference to the reaction of 2,2-bis (4-hydroxylphenol) propane (usually called bisphenol-A) with epichlorohydrin.

Since these diglycidyl ethers are generally called liquid epoxy resins, this terminology will be used in the description which follows.

2. Description of the Prior Art

The liquid epoxy resins form products which find many technical applications. For example, they are used in the field of varnishes and coatings in general or in the field of adhesives or agglomerates (cement or asphalt pavements).

These resins also find many applications in the electronic field (casting, printed circuits, sealing and encapsulation of electrical components) as well as in many other fields.

For certain applications, liquid epoxy resins of high purity are required, especially with regard to the content of organic or inorganic halogens, and in particular, hydrolyzable or non-hydrolyzable chlorine, which must be reduced to negligible values.

Such resins are particularly useful for special applications such as varnishes with a high resistance to chemical and atmospheric agents, and in the production of insulators and laminated electric condensers for printed circuits and for the encapsulation of electrical components. Technical processes are known for producing liquid epoxy resins from bisphenol-A and epichlorohydrin, either by a continuous or a discontinuous process, operating in the presence of an alkali metal hydroxide in quantities of 2 moles, or about 2 moles, for every mole of bisphenol-A.

In the discontinuous process, the normal procedure is to feed a concentrated acqueous solution of alkali metal hydroxide to a solution of bisphenol-A in epichlorohydrin. Such processes are, moreover, carried out at atmospheric or slightly lower than atmospheric pressure, controlling the temperature so as to distil continuously the water introduced with the alkali metal hydroxide, as an azeotropic mixture with the epichlorohydrin. When the addition of the solution of alkali metal hydroxide has been completed all the water is removed, the unreacted epichlorohydrin is recovered by distillation at pressures lower than atmospheric, and the alkali metal chloride, a sub-product of the reaction, is separated by dissolving in water.

The liquid epoxy resins obtained in this manner typically have a high viscosity, an undesirable colour, and because of their relatively high chlorine content, are not suitable for those special applications which have been previously mentioned. In fact by operating in the manner previously described, a liquid epoxy resin is obtained with a residual chlorine content of the order of 0.5 – 0.8% by weight.

Methods of producing liquid epoxy resins by a continuous process, by effecting the reaction of the bisphenol-A with the epichlorohydrin in a number of reactors installed in series are also know in the art. More particularly, in accordance with such processes, the bisphenol-A and the epichlorohydrin are continuously fed to the first of such reactors, while the alkali metal hydroxide in aqueous solution is introduced into each reactor up to a maximum quantity equal, or about equal to 2 moles for every mole of bisphenol-A. The reaction products, which are discharged continuously from the last reactor, are subjected to decantation to separate the liquid epoxy resin from the water and the alkali metal chloride which is a sub-product of the reaction.

A characteristic peculiar to these conventional processes is to carry out the reaction in the presence of oxygenated organic substances of alcoholic or ketonic nature. However, this procedure is disadvantageous, either because the presence of extraneous substances always causes a decrease in the purity of the resin produced, or because reactive substances such as the alcohols or the ketones can give rise to secondary reactions with formation of unwanted sub-products. In every case, there is the problem relating to the separation of the added substances from the liquid epoxy resin, as well as the necessity to purify such added substances before recycling them to the reaction medium.

A further disadvantage of the processes described, is the difficulty in separating the liquid epoxy resin from the water and the alkali metal halide which is a sub-product of the reaction. In fact, the difficulty and the lack of spontaneity in the separation of liquid epoxy compounds from water or aqueous saline solutions, is well known.

In order to facilitate this separation, substances capable of varying the interface tension or the density have been used in the art. However, the addition of such extraneous substances to the system causes a decrease in the purity of the resin, notwithstanding the fact that the removal of these substances often proves to be very difficult. On the other hand, when operating without these extraneous substances, lengthy periods of decantation at elevated temperature are necessary, and this normally gives rise to undesirable secondary reactions.

It is known that the formation of the liquid epoxy resins is effected by a coupling reaction between the epichlorohydrin and the bisphenol-A, followed by a dehydrochlorination reaction of the alpha-chlorohydrin thus produced.

As known, the latter is an equilibrium reaction, and this involves, at the end of the reaction, the presence of a certain quantity of free alkali metal hydroxide which promotes unfavourable secondary ramification reactions. The use, conventional in the art, of acids or acid salts to neutralize the free basicity can lead, as is known, to hazardous "interaction reactions" between the acids and the epoxy bridge of the resin.

The liquid epoxy resins produced by the described processes have a total content of hydrolyzable and non-hydrolyzable chlorine such as to make these resins unsuitable for some applications.

The quantity of non-hydrolyzable chlorine present in the liquid resin is a function of the reaction conditions and a reduction in the content of hydrolyzable chlorine can be obtained by using in the reaction medium, a quantity of alkali metal hydroxide greatly in excess of the aforesaid quantity. However, this favours the secondary reactions previously alluded to.

Moreover, it has been noted that when operating in the presence of an excess of epichlorohydrin and also possibly in the presence of added alcoholic or ketonic solvents, or other types of solvents, it was possible to reduce the content of hydrolyzable chlorine to acceptable values, solely by the use of an excess of alkali metal hydroxide such as will impair the characteristics of the liquid epoxy resin.

SUMMARY OF THE INVENTION

It has been found that it is now possible to eliminate, or at least, to substantially reduce the disadvantages of the prior art, by means of the process of the present invention which makes it possible to obtain diglycidyl ethers of dihydroxy phenols (or liquid epoxy resins) of high purity, practically free of hydrolyzable chlorine and with a virtually nil content of non-hydrolyzable chlorine.

Thus, the invention provides a process for the continuous preparation of diglycidyl ethers of dihydroxy phenols (liquid epoxy resins) by reacting a dihydroxy phenol with an epihalohydrin in the presence of an alkali metal hydroxide, characterized by:

contacting in a first stage of reaction a dihydroxy phenol with an excess of epihalohydrin and an aqueous solution of alkali metal hydroxide in a molar ratio of the hydroxide to the phenol not exceeding 2:1, at a pressure higher than atmospheric and at a temperature higher than ambient temperature;

subjecting the reaction products of the first stage to decantation and washing with water, at a pressure above atmospheric pressure and at a temperature above ambient temperature and recovering the resulting organic phase;

removing the reacted epihalohydrin from the organic phase by distillation at subatmospheric pressure and recovering as a residue a liquid epoxy resin having a content of hydrolyzable chlorine of from 1 to 6% by weight;

dissolving the recovered epoxy resin in a hydrocarbon and contacting in a second stage of reaction the resulting solution with an aqueous solution of alkali metal hydroxide while maintaining an atomic ratio of alkali metal to the hydrolyzable chlorine contained in the resin of from 1:1 to 1.17:1, at a pressure above atmospheric pressure and at a temperature above ambient temperature;

subjecting the reaction products of the second stage to decantation and washing with water, at a pressure above atmospheric pressure and a temperature above ambient temperature and recovering the resulting separated organic phase;

removing by distillation at subatmospheric pressure the hydrocarbon solvent from the organic phase and recovering a liquid epoxy resin with a content of hydrolyzable chlorine less than 0.02% by weight.

Operating in the conditions of the process of the invention, liquid epoxy resins are obtained which are free of sub-products and having a content of hydrolyzable chlorine always less than 0.02% and generally of the order of from 0.01 to 0.001% in weight.

BRIEF DESCRIPTION OF THE ACCOMPANYING DRAWING

The drawing shows schematically an apparatus used in the examples.

DETAILED DESCRIPTION OF THE INVENTION

In the following description the process for the preparation of the liquid epoxy resins will be described with reference to the reaction of bisphenol-A with epichlorohydrin.

In this manner, according to the process of the invention, the bisphenol-A, in the first stage of reaction, is contact with an excess of epichlorohydrin and generally with a quantity of 8 to 15 moles of epichlorohydrin for every mole of bisphenol-A. The best results are obtained with a quantity of epichlorohydrin of the order of 10 moles for every mole of bisphenol-A.

In the first stage an alkali metal hydroxide (preferably, sodium or potassium is also fed in quantities equivalent to the phenolic hydroxyl groups of the bisphenol-A, or less than this equivalent quantity, and at any rate, sufficient to ensure in the discharged resin a content of hydrolyzable chlorine of from 1 to 6% by weight.

In fact, it has been found that when the content of hydrolyzable chlorine is reduced to values lower than 1% by weight, operating in a medium rich in epichlorohydrin, molar ratios of alkali metal hydroxide to bisphenol-A somewhat higher than 2:1 are required, and in these conditions, there are secondary reactions with formation of undesirable sub-products. Furthermore, it is not convenient to keep the content of hydrolyzable chlorine at values greater than 6% by weight, in the resin discharged at the first stage, because such products are unsuitable for treatment in the second stage of the present invention.

The best results are obtained, if, in the first stage of reaction, liquid epoxy resins having a content of hydrolizable chlorine of the order of 3% by weight, are discharged.

In practice, if it is desired to obtain a resin with a content of hydrolyzable chlorine of the order of 1% by weight, in the first stage of the present invention, alkaline hyroxide is fed in, in a molar ratio of hydroxide to bisphenol-A, of the order of 2:1. If, instead, a greater chlorine content is required, the amount of alkali metal hydroxide is proportionally reduced. Thus, for example, liquid epoxy resins having a content of hydrolyzable chlorine of the order of 6% by weight, can be obtained by using approximately 0.62 moles of alkali metal hydroxyl group for each phenolic hydroxide of the bisphenol-A, i.e., approximately 1.24 moles of hydroxide for each mole of bisphenol-A.

Furthermore, the alkali metal hydroxide is fed, in the first reaction stage, in the form of an aqueous solution, and it is convenient to use solutions with a content of hydroxide of about 10 to 50% by weight.

Preferably, the first stage is carried out at a pressure of 1 to 4 atmospheres higher than atmospheric pressure, at a temperature of from 80° to 140° C, and with a residence time of from 20 to 140 minutes.

In a preferred embodiment of the process of the present invention, the reagents are fed at the top of an elongate vertical reaction zone, and the mixture is made to flow continuously from top to bottom. For this purpose, it is useful to have reactors of a high length-/diameter ratio such as, for example, from 6:1 to 15:1. Preferably, cylindrical towers are used, the the reagents mixture is subjected to agitation while it flows towards the bottom of the reactor.

It should be noted that the alkali metal hydroxide can be fed either wholly at the top of the reactor, or only partly, and in the latter case, the remaining fraction is fed at one or more points along the body of the reactor.

It has also been established that the system and degree of agitation are important factors. In fact, particularly satisfactory results are obtained when agitation in the reactor is normal or prevailingly normal, with respect to the vertical axis of the reactor. To this end, it is possible to use agitators with oriented blades, turbine, agitators, propeller agitators or similar, and it is also convenient to keep the speed of the agitator at from 80 to 200 r.p.m.

In these conditions a mass flow is achieved within the reactor, of the type known as "piston-flow" and consequently, the composition of the mass varies continuously from the head to the foot of the reactor.

The products discharged from the first stage are subjected to continuous decantation in a decantation vessel. Generally, this vessel is kept at a pressure of 1 to 4 atmospheres above atmospheric pressure and the decantation temperature is maintained in a range of from 40°–50° C up to a limit of 140° C and preferably at a value of the order of 90°–100° C. Surprisingly enough, an immediate and complete separation is achieved when during decantation a pressure higher than atmospheric is maintained.

In this manner the use of substances capable of varying the interface tension or the density are avoided, and likewise, the long periods of decantation at elevated termperature which lead to disadvantageous results.

According to the present invention the organic phase containing the liquid epoxy resin obtained by decantation is subjected to continuous washing in water, operating within the same range of temperatures and pressures as indicated for decantation. Because of the operating pressure, an immediate and complete separation between the aqueous phase and the solution of epoxy resin in epichlorohydrin is also achieved in this case.

According to a preferred embodiment, the reaction products of the first stage are subjected to simultaneous washing and decantation in one and the same zone. This is made possible because of the ease of separation when operation is under the previously mentioned conditions, particularly the pressure conditions.

In every case, the washing water is introduced in an amount sufficient to dissolve the alkali metal chloride which is a sub-product of the reaction, and best results are obtained by controlling the amount of washing water in order to obtain an aqueous phase with a pH of from 7.5 to 8.

By means of the washing carried out in the indicated conditions, the liquid epoxy resin is freed from all water-soluble components. In this manner, not only is the alkali metal chloride removed, but also the unreacted alkali metal hydroxide, without using those acids or acid salts which can be detrimental to the resin.

The organic phase containing the liquid epoxy resin and the unreacted epichlorohydrin coming from the decantation, contains an amount of water of about 1.5% by weight. This small percentage of water can easily be eliminated by feeding the organic phase into a medium kept at a lower pressure than that of the decantation, for example at atmospheric pressure. In this manner the evaporation of the water is effected in the form of an azeotrope with the epichlorohydrin and the anhydrous product is recovered, from which the unreacted epichlorohydrin is then removed. To this end the epichlorohydrin is continuously distilled at a pressure lower than atmospheric, for example at 5–40 mmHg, and preferably by means of the thin film method.

The residue of the distillation comprises the liquid epoxy resin having a content of hydrulyzable chlorine of from 1 to 6% by weight. According to the process of the present invention the liquid epoxy resin is dissolved in a hydrocarbon solvent and the solution thus obtained is contacted with an aqueous solution of alkali metal hydroxide in the second stage of the reaction.

Hydrocarbon solvents useful for the purpose are typically those which are liquid at the operating conditions, insoluble or barely soluble in water, and are generally chosen from aromatic hydrocarbons or cycloaliphatic hydrocarbons. Not entirely satisfactory results are obtained when using aliphatic hydrocarbons.

The preferred solvents are cyclohexane, xylene, benzene, or at any rate aromatic solvents with a boiling point of less than 160° C and with a solubility parameter comprised within the range of values of $\overline{8 \text{ to } 11}$, the solubility parameter being defined by $\sqrt{\Delta E/V}$ where $\Delta E$ is the heat of evaporation and V the molar volume. The liquid epoxy resin coming from the first stage is generally dissolved in the selected solvent to a concentration of from 30 to 80% by weight, and the resulting solution is contacted with an aqueous solution of alkali metal hydroxide, the hydroxide being used in quantities stoichiometrically equal or up to 17% higher, relatively to the content of hydrolyzable chlorine in the resin.

In this case too, it is convenient to use aqueous solutions with an alkali metal hydroxide concentration of about 10 to 50% by weight.

The second stage is usually carried out at a pressure of from 1 to 4 atmospheres higher than atmospheric, at a temperature of from 80° to 140° C and with a contact time of from 10 to 80 minutes.

Moreover, it is convenient to use an elongated vertical reaction zone, provided with means for lateral agitation, or mostly lateral, so as to achieve an operation of the "piston-flow" type, that is to say, similar to that described for the first stage of the reaction. In practice, the solution of the resin in, the hydrocarbon is fed continuously at the top of an elongated vertical reactor, whereas the alkali metal hydroxide can be fed at the top entirely or only in part; in the latter case, the remaining fraction is fed at one or more points along the body of the reactor.

In every case, at the foot of the reactor, there is a continuous discharge of the reaction products which contain a liquid epoxy resin with a titre of hydrolyzable chlorine always less then 0.02% by weight, and generally of the order of 0.01 to 0.001% by weight, and this as a function of the quantity of alkali metal hydroxide used.

Moreover, the content in non-hydrolyzable chlorine is always less than 0.2% and generally of the order of 0.1 –0.15% by weight.

In practice, in the second stage of reaction a complete dehydrochlorination is achieved, operating at a pressure higher than atmospheric, at a relatively elevated temperature and with relatively short periods of contact. Under these conditions, the epoxy resin is in no way damaged.

The products discharged from the second stage of the reaction are subject to continuous washing and decantation. These operations are conveniently carried out at a pressure of 1 to 4 atmospheres higher than atmospheric, at a temperature not exceeding 140° C and preferably of the order of 90°–100° C. The decantation and the washing can take place in two distinct zones; in a preferred embodiment, they take place simultaneously and in the same zone.

In every case a practically instantaneous separation of the aqueous and organic phases is achieved.

The quantity of water used for the washing must be at least equal to that required for the complete dissolving of the alkali metal chloride and the best results are obtained when the pH of the resulting aqueous phase has a value of 7.2–7.5.

The organic phase separated by decantation contains a small quantity of water which can be eliminated by feeding this phase into a zone which is kept at a pressure lower than that of the decantation, for example, atmospheric pressure. In this manner, the water is vaporized together with a small quantity of organic solvent and the anhydrous organic phase in subjected to distillation at a pressure lower than atmospheric, for example, from 5 to 40 mmHg. Preferably a thin film evaporator is used for the purpose.

A liquid epoxy resin having a chlorine content within the range of values previously indicated, and with other characteristics within the following ranges of values:
Epoxy value $=0.48 -0.53$.
Viscosity $=X -Z_2$. is obtained in this manner, as a residue of the distillation.

The viscosity is expressed in accordance with the Gardner scale and is determined by dissolving the resin in butyl-carbitol with a concentration of 90% resin.

The content of hydrolyzable chlorine is determined in accordance with Norm ASTM D 1726/72T.

The epoxy value is expressed in epoxy moles contained in 100 grams of liquid epoxy resin and is determined according to Norm ASTM D 1652/62T.

The process of the present invention has been described with reference to the reaction of bisphenol-A with epichlorohydrin.

However, it is possible to use other epihalohydrins, different from epichlorohydrin, for example, epibromohydrin and methyl-epichlorohydrin.

Moreover it is possible to use diphenols different from bisphenol-A, such as mononuclear or polynuclear dihydroxy phenols.

Examples of such phenols are: catechol, resorcinol, 2-methyl resorcinol, quinol, 2-chloroquinol, 1,5-dihydroxynaphthalene, 4,4'-dihydroxybiphenyl, bis(p-hydroxyphenyl) methane, 1,1-bis(p-hydroxyphenyl)ethane and the like.

The following experimental examples will serve to further describe the invention without, however, limiting it in any way.

In these examples, the parts and percentages are given by weight unless otherwise specified.

EXAMPLE 1

The apparatus used is of the type schematically shown in the accompanying drawing.

In the drawing, 1 indicates a first stage reactor, consisting of a cylindrical tower having a height/diameter ratio of 11:1, provided with a blade agitator 31 which is made to rotate at a speed of 150 r.p.m.

To the head of the reactor 1, through line 7, there is fed continuously a solution of bisphenol-A in epichlorohydrin, and more precisely, 684 parts of bisphenol-A per hour and 2775 parts of epichlorohydrin per hour.

Through line 8 296 parts per hour, of an aqueous solution of sodium hydroxide at 50% is fed.

This solution is introduced into the reactor at three distinct points through the lines 9, 10, 11.

More precisely, through the line 9, at the top of the reactor there is introduced 13.5%, of the solution of sodium hydroxide, through the line 10, at about mid-height of the reactor there is fed 33.8% of the solution and through line 11, at a height about ⅓ from the bottom of the reactor there is fed 52.7% of the solution.

The reactor 1 is moreover operated at a pressure of 4 atmospheres, at a temperature of 95° C, and the residence time is of 100 minutes.

The reaction products are continuously discharged from the reactor 1, through the line 12 and are fed to a decantation vessel 5 where washing of the resin is effected. More particularly, the decantation vessel 5 is operated at 90° C, at a pressure about equal to that of reactor 1, and there are fed 400 parts per hour of water through the line 13, at a level of the decantation vessel about equal to that of the discharge outlet of the line 12.

In the decantation vessel 5 there is separated almost instantaneously an aqueous phase which is discharged through the line 14, and an organic phase which is first dehydrated by being passed into a zone kept at atmospheric pressure (not shown in the Figure) and then fed to the thin film evaporator 2 through the line 15.

The evaporator 2 is operated at a temperature of 160° C, at a pressure of 10 mmHg and the unreacted epichlorohydrin is removed through the line 16.

Through the line 17 about 1.080 parts per hour of liquid epoxy resin are recovered with an epoxy equivalent of 305, a content of hydrolyzable chlorine of 5.9% by weight and a viscosity of $Z_3+$ measured in a 90% solution of butyl carbitol.

This opoxy resin is continuously fed to the head of the reactor 3 (similar to reactor 1) together with 725 parts per hour of toluene fed through the line 18. To reactor 3, through the line 19, there are fed 161 parts per hour of a 50% aqueous solution of sodium hydroxide. Moreover, the reactor, 3 is operated at a temperature of 90° C, at a pressure of 3 atmospheres and with a time of contact equal to 30 min evaporator 4. The evaporator 4 is operated at a temperature of 165° C, at a pressure of 15 mmHg, and the toluene is removed through the line 24.

Through the line 25 there are recovered 1010 parts per hour of liquid epoxy resin having the following characteristics:

| | |
|---|---|
| - Epoxy value | = 0.5 |
| - Hydrolyzable chlorine | = 0.01% |

-continued

| - Non-hydrolyzable chlorine | = 0.12% |
|---|---|
| - Viscosity | = $Z_1+$ |

EXAMPLE 2 (comparison)

The process is carried out as in Example 1 with the difference that the reaction products of the first stage (reactor 1), are fed (after dehydration and washing) directly to the second stage (reactor 3).

For this reason, the excess epichlorohydrin is not eliminated between the first and second stage and toluene is not added. Instead, the epichlorohydrin is removed in the evaporator 4 from the products discharged from the second stage of the reaction.

With regard to the other conditions, the operation is carried out in the manner described in the first Example.

An epoxy liquid resin is obtained having the following chracteristics:

| - Epoxy value | = 0.43 |
|---|---|
| - Hydrolyzable chlorine | = 3.2% |
| - Non-hydrolyzable chlorine | = 0.11% |
| - Viscosity | = $Z_2+$ |

EXAMPLE 3 (comparison)

The process is carried out as in Example 2, feeding the reactor 3 with sodium hydroxide in a 50% aqueous solution, in a quantity equal to 300 parts per hour.

A liquid epoxy resin is obtained having the following characteristics:

| - Epoxy value | = 0.45 |
|---|---|
| - Hydrolyzable chlorine | = 0.88% |
| - Non-hydrolyzable chlorine | = 0.11% |
| - Viscosity | = $Z_1+$ |

EXAMPLE 4 (comparison)

The process is carried out as in Example 1 with the difference that the excess of epichlorohydrin is not eliminated from the reaction products of the first stage (reactor 1) and there are added (after washing and dehydration) 570 parts per hour of toluene through line 18. The mixture obtained in this manner is fed to the second stage (reactor 3).

The excess epichlorohydrin and the toluene are eliminated from the products discharged by reactor 3, in the evaporator 4.

The other conditions are kept the same to those described in Example 1.

There is obtained a liquid epoxy, resin having the following characteristics:

| - Epoxy value | = 0.43 |
|---|---|
| - Hydrolyzable chlorine | = 3.1% |
| - Non-hydrolyzable chlorine | = 0.5% |
| - Viscosity | = $Z_2+$ |

EXAMPLE 5 (comparison)

Operating as in Example 4, the reactor 3 is fed, through the line 19, with a 50% aqueous solution of sodium hydroxide at the rate of 304 parts per hour.

An epoxy liquid resin is obtained having the following characteristics:

| - Epoxy value | = 0.47 |
|---|---|
| - Hydrolyzable chlorine | = 0.72% |
| - Non-hydrolyzable chlorine | = 0.5% |
| - Viscosity | = $Z_1+$ |

EXAMPLE 6

Operating as in Example 1, 300 parts per hour of aqueous sodium hydroxide at 50% by weight are fed through the line 8.

Keeping the other conditions as in Example 1, a liquid epoxy resin is obtained of the following characteristics:

| - Epoxy value | = 0.5 |
|---|---|
| - Hydrolyzable chlorine | = 0.001% |
| - Non-hydrolyzable chlorine | = 0.12% |
| - Viscosity | = $Z_1$ |

EXAMPLE 7

Operating as in Example 1, there are fed to the reactor 1, through the line 7, 684 parts per hour of bisphenol-A and 2775 parts per hour of epichlorohydrin.

Through the line 8 there are fed 400 parts per hour of a 50% aqueous solution of sodium hydroxide. This solution is divided up through the lines 9, 10 and 11 in the percentages indicated in Example 1. Through the line 15, 2700 parts per hour of a 40% solution of epoxy resin in epichlorohydrin are recovered.

The latter is separated in the evaporator 2, and through the line 17 there is discharged a liquid epoxy resin having the following characteristics:

| - Epoxy value | = 0.46 |
|---|---|
| - Hydrolyzable chlorine | = 3.2% |
| - Non-hydrolyzable chlorine | = 0.13% |
| - Viscosity | = $Z_2+$ |

This resin is fed to the reactor 3 together with toluene, supplied through the line 18 at a rate of 725 parts per hour.

Through the line 19 are fed 83 parts per hour of a 50% aqueous solution of sodium hydroxide. Proceeding as described in Example 1, there is recovered through the line 25 at a rate of 1007 parts per hour a liquid epoxy resin having the following characteristics:

| - Epoxy value | = 0.51 |
|---|---|
| - Hydrolyzable chlorine | = 0.002% |
| - Non-hydrolyzable chlorine | = 0.13% |
| - Viscosity | = $Z+$ |

EXAMPLE 8 (comparison)

The procedure is the same as in Example 7 with the difference that the reaction products of the first stage (reactor 1) are fed (after washing and dehydration) directly to the second stage (reactor 3).

Therefore, the excess epichlorohydrin is not eliminated between the first and second stage and toluene is not added.

Instead, the epichlorohydrin is eliminated in the evaporator 4 from the products discharged from the second reaction stage.

The second stage (reactor 3) is fed through line 19 with a 50% aqueous sodium hydroxide, at a rate of 83 parts per hour.

The other conditions are kept as in Example 7.

A liquid epoxy resin is obtained having the following characteristics:

| | | |
|---|---|---|
| - Epoxy value | = | 0.45 |
| - Hydrolyzable chlorine | = | 1.2% |
| - Non-hydrolyzable chlorine | = | 0.13% |
| - Viscosity | = | $Z_2$ |

EXAMPLE 9 (comparison)

The procedure is the same as in Example 8 with the only difference that the aqueous sodium hydroxide at 50% is fed to the reactor 3 at a rate of 128 parts per hour.

A liquid epoxy resin is obtained of the following characteristics:

| | | |
|---|---|---|
| - Epoxy value | = | 0.47 |
| - Hydrolyzable chlorine | = | 0.65% |
| - Non-hydrolyzable chlorine | = | 0.13% |
| - Viscosity | = | $Z_2$ |

EXAMPLE 10 (comparison)

The procedure is the same as in Example 7 with the difference that the excess epichlorohydrin is not removed from the reaction products of the first stage (reactor 1) and there are added (after washing and dehydration) 485 parts per hour of toluene through the line 18. The resulting mixture is fed to the second stage (reactor 3).

The excess epichlorohydrin and the toluene are removed in the evaporator 4 from the products discharged from the reactor 3.

The other conditions are kept as in Example 7.

A liquid epoxy resin is obtained having the following characteristics:

| | | |
|---|---|---|
| - Epoxy value | = | 0.46 |
| - Hydrolyzable chlorine | = | 1.1% |
| - Viscosity | = | $Z_1 +$ |

EXAMPLE 11

Operating as in Example 7, the reactor 1 is fed through the line 8 with 440 parts per hour of aqueous sodium hydroxide at 50% and there is discharged from the first reaction stage a liquid epoxy resin having the following characteristics:

| | | |
|---|---|---|
| - Epoxy value | = | 0.47 |
| - Hydrolyzable chlorine | = | 1.1% |
| - Non-hydrolyzable chlorine | = | 0.18% |
| - Viscosity | = | $Z_2$ |

Operating as described in Example 7, the resin is dissolved in toluene supplied at a rate of 725 parts per hour and the resulting mixture is fed to the reactor 3, where it comes in contact with 26 parts per hour of aqueous sodium hydroxide at 50%.

Always proceeding as described in Example 7, a liquid epoxy resin is discharged, having the following characteristics:

| | | |
|---|---|---|
| - Epoxy value | = | 0.51 |
| - Hydrolyzable chlorine | = | 0.003% |
| - Non-hydrolyzable chlorine | = | 0.18% |
| - Viscosity | = | $Z +$ |

We claim:

1. A method for the continuous preparation of liquid epoxy resins comprising diglycidyl ethers of dihydroxy phenols by reacting a dihydroxy phenol with an epihalohydrin in the presence of an alkali metal hydroxide, which comprises:

contacting in a first stage of reaction a dihydroxy phenol with an excess of epihalohydrin in a quantity of from 8 to 15 moles of said epihalohydrin for each mole of said dihydroxy phenol and an aqueous solution of alkali metal hydroxide in a molar ratio of said hydroxide to said dihydroxy phenol not exceeding 2:1, at a pressure of from 1 to 4 atmospheres above atmospheric pressure, at a temperature of from 80° to 140° C and with a residence time of from 20 to 140 minutes;

subjecting the reaction products of said first stage to decantation and washing with water, at a pressure of from 1 to 4 atmospheres above atmospheric pressure and at a temperature of from 40° to 140° C and recovering the resulting organic phase;

removing the unreacted epihalohydrin from said organic phase by distillation at subatmospheric pressure and recovering as a residue a liquid epoxy resin having a content of hydrolyzable chlorine of from 1 to 6% by weight;

dissolving said recovered epoxy resin in an aromatic hydrocarbon or a cycloaliphatic hydrocarbon and contacting in a second stage of reaction the resulting solution with an aqueous solution of alkali metal hydroxide while maintaining an atomic ratio of alkali metal to the hydrolyzable chlorine contained in the resin of from 1:1 to 1.17:1, at a pressure of from 1 to 4 atmospheres above atmospheric pressure, at a temperature of from 80° to 140° C and with a contact time of from 10 to 80 minutes;

subjecting the reaction products of said second stage to decantation and washing with water, at a pressure of from 1 to 4 atmospheres above atmospheric pressure and at a temperature of from ambient temperature to 140° C and recovering the resulting separated organic phase; and removing by distillation at subatmospheric pressure the hydrocarbon solvent from said organic phase and recovering a liquid epoxy resin with a content of hydrolyzable chlorine less than 0.02% by weight.

2. The method of claim 1, wherein said dihydroxy phenol is bisphenol-A, said epihalohydrin is epichlorohydrin and said alkali metal hydroxide is sodium hydroxide or potassium hydroxide.

3. The method of claim 1, wherein said aqueous solution used in the first and the second stage contains from 10 to 50% by weight of alkali metal hydroxide.

4. The method of claim 1, in which the first stage of reaction and the second stage of reaction are carried out in an elongated vertical reaction zone wherein the reaction mixture is agitated and made to flow continuously from top to bottom with a movement of the "pistonflow" type.

5. The method of claim 1 wherein said unreacted epihalohydrin is removed at a pressure of from 5 to 40 mm Hg, by means of the thin film method.

6. The method of claim 1, wherein the hydrocarbon solvent is selected from the group consisting of cyclohexane, toluene, xylene, benzene and aromatic hydrocarbons having a boiling point not exceeding 160° C and a solubility parameter of from 8 to 11.

7. The method of claim 1, wherein said solution of epoxy resin in a hydrocarbon contains from 30 to 80% by weight of resin.

8. The method of claim 1, in which said hydrocarbon solvent is removed at a pressure of from 5 to 40 mm Hg by means of the thin films method.

* * * * *